(12) United States Patent
Cooper et al.

(10) Patent No.: US 6,342,036 B1
(45) Date of Patent: Jan. 29, 2002

(54) SELF-RETAINING VAGINAL RETRACTOR

(76) Inventors: Cheryl A. Cooper; Linda A. Bates, both of 10,001 Meandering Way, Fort Smith, AR (US) 72903

( * ) Notice: Subject to any disclaimer, the term of this patent is extended or adjusted under 35 U.S.C. 154(b) by 0 days.

(21) Appl. No.: 09/776,433

(22) Filed: Feb. 2, 2001

(51) Int. Cl.[7] ............................................... A61B 17/02
(52) U.S. Cl. ...................................... 600/224; 600/232
(58) Field of Search ................................. 600/232, 224, 600/219, 222, 220, 233

(56) References Cited

U.S. PATENT DOCUMENTS

| | | | | |
|---|---|---|---|---|
| 475,975 A | * | 5/1892 | Clough | 600/224 |
| 1,707,689 A | * | 4/1929 | Sloan | 600/233 |
| 1,839,726 A | * | 1/1932 | Arnold | 600/233 |
| 1,963,173 A | * | 6/1934 | Morin | 600/233 |
| 2,812,759 A | * | 11/1957 | Taylor | 600/232 |
| 3,522,799 A | * | 8/1970 | Gauthier | 600/233 |
| 3,724,449 A | * | 4/1973 | Gauthier | 600/233 |
| 5,755,660 A | * | 5/1998 | Tyagi | 600/232 |
| 5,944,658 A | * | 8/1999 | Koro et al. | 600/232 |

* cited by examiner

*Primary Examiner*—Paul J. Hirsch
(74) *Attorney, Agent, or Firm*—Jerry L. Mahorin

(57) ABSTRACT

The self-retaining vaginal retractor comprises an inverted-U-shaped slotted base plate. A top and pair of cooperating side vagina retracting blades are selectively, removably and adjustably secured to the base plate. Each blade comprises a curved tongue portion and an integral slotted handle portion. The blades are secured by adjustably tensionable fasteners extending through the slots. The blades are adjustable both horizontally and vertically. An optional bag is selectively removably secured to snap fasteners mounted on the base. The bag comprises a top portion and a pair of side portions coinciding with the base. A lower portion extends downward from the side portions defining a pouch to hold the blades and fasteners, and catch debris and fluid. Preferably, the fastener comprises a carriage bolt indexed to a slot in the base, extending through a slot in a blade handle and a wing nut.

18 Claims, 8 Drawing Sheets

SELF-RETAINING VAGINAL RETRACTOR

BACKGROUND OF THE INVENTION

1. Field of the Invention

The present invention broadly relates to medical devices and gynecological instruments. Specifically, the present invention is a Self-Retaining Vaginal Retractor used to dilate the vaginal cavity for surgical and examination procedures. Art pertinent to the subject matter of the present invention can be found in various Subclasses of United States Patent Class 600, including Subclasses 220 through 224.

2. Description of the Prior Art

Numerous patents have been issued on surgical and examination instruments. Devices for retracting the vaginal cavity for gynecological procedures include medical or surgical instruments known variously as retractors or speculums.

Perez, U.S. Pat. No. 4,597,382; Beck, U.S. Pat. No. 5,499,964; Dickie, U.S. Pat. No. 5,231,973; Patton, U.S. Pat. No. 5,505,690; and, Lundberg, U.S. Pat. No. 5,318,010 disclose speculums having a "pistol grip" configuration. These speculums have "bill" shaped blades and once deployed define openings between the blades.

A single bar frame mounting a fixed retractor and a sliding retractor is disclosed in Forder, U.S. Pat. No. 4,344,420. An adjustable, frame mounting a pair of retractors is disclosed in Smith, U.S. Pat. No. 1,706,500. Both of these are specifically intended for use in abdominal surgery. A ring mounted, four blade, Speculum is disclosed in Van Meter, U.S. Pat. No. 497,064. The handles for the speculums extend through slots defined in the ring and the speculums are held in an extended position by a pawl-and-rack arrangement anchored to the ring. Pisarik, U.S. Pat. No. 6,024,697, discloses a three blade speculum having a hinged frame and ratchet mechanism for holding it open. A base mounting a rather complicated retractor opening mechanism is presented in Villalta, U.S. Pat. No. 5,183,032. This device uses a cam and set of arms to deploy four retractor blades. The vaginal dilator disclosed in Holland, U.S. Pat. No. 605,547 employs a base mounted, U-shaped frame to mount three spring-loaded speculum blades. An open-ended frame for a speculum is disclosed in Burgin, U.S. Pat. No. 4,156,424. The width of the frame is adjustable and the height of the speculum blades is adjustable as well.

Grieshaber and Gauthier U.S. Pat. Nos. 2,693,795 and 3,384,077, are retractors, primarily intended for abdominal surgery. Each discloses a blade mounted on a slotted handle. The blades are slidably mounted to the frames through the slots. The vaginal speculum disclosed in Rose, U.S. Pat. No. 3,985,125, is a "bill" type, pistol grip speculum which has a pair of slots defined in the sides of one member to allow the blades to be slid apart as well as hinged apart. Similarly, a bill/pistol-grip speculum using slots is disclosed in Jamieson, U.S. Pat. No. 4,323,057. Here the slots are in the back of the speculum handles, once again allowing the blades to be slid apart as well as hinged apart. A pistol grip speculum with sidewall support blades is disclosed in Hoftman, U.S. Pat. No. 6,024,696. A slot in the handle allows the hinged top and fixed bottom blade to be slid apart. Another four-blade speculum is shown in Weiss, U.S. Pat. No. 5,868,668. This is another pistol grip speculum with side blades and a thumb-operated lever.

An adjustable rectangular framed retractor for vaginal surgery is illustrated in Mahmoodian, U.S. Pat. No. 4,924,857. Palmer, U.S. Pat. No. 1,030,530 discloses a two bladed speculum mounted to a slotted frame, which also employs a plate mounted on a threaded rod. The plate is intended to bear on the symphisis pubis to hold the speculum in place. A pair of single blade, slotted frame, bearing plate retractors for vaginal surgery are presented by Richmond, U.S. Pat. No. 3,709,215 and Rizvi, U.S. Pat. No. 6,120,438. The bearing plate in Richmond bears against the suprapubic area of the abdomen, while the plate in Rizvi is positioned under the patient. A three bladed speculum employing a lower blade extending from a slotted frame and two upper/side blades is disclosed in Guttman, U.S. Pat. No. 2,374,863.

Use of retractors having upper and side blades in a single instrument for a hysterectomy is problematic due to the mechanism obstructing the Surgeon's operating space. Additionally, such devices are cumbersome.

Conventionally, separate upper, side and lower manual retractors are employed for vaginal procedures. A conventional lower retractor is a weighted vaginal speculum, which maintains stretching action through gravity. The conventional upper retractor protects and supports the urethra and urinary bladder and also gives the Surgeon more exposure and operating space.

Heretofore, the upper and side retractors have been L-shaped right angle instruments with a long upwardly extending handle which is held in place manually, although their position is virtually static. Constant force of only a pound or two in an upward, or outward direction is required to maintain retraction. The task of holding the upper retractor is very difficult and tiring because it must be held in place from thirty minutes to over an hour in some cases. Furthermore, when the patient is positioned for vaginal procedures, her thighs and legs are in the way of an Assistant standing on either side of the operating table. On the other hand, if the Assistant holding the upper retractor sits beside the Surgeon it is still difficult because of the crowded conditions resulting from three people sitting and working between the patient's legs. Assistants must, at intervals, use both hands in aiding the Surgeon. As a result, the task of holding a retractor then temporarily occupies one of the instrument Assistants' busy hands.

The prior art fails to disclose a multi-bladed self-retaining vaginal retractor in which each of the blades are independently adjustable both vertically and horizontally. Hence, it is desirous to provide a Self-Retaining Vaginal Retractor which has adjustably mounted blades which can be multi-directionally manipulated to provide a Surgeon relatively free access to the uterus of a patient.

SUMMARY OF THE INVENTION

My invention is an improved and simple to use self retaining anterior and side retractor for vaginal procedures and surgery. The present retractor comprises four major parts, which are adjustable in relation to each other to fit the anatomy of the patient. An inverted U-shaped frame, with three slotted openings, which mounts an upper and two side vagina retracting blades using adjustable fasteners.

To use my self-retaining vaginal retractor a patient's legs are flexed in the lithotomy position for the performance of vaginal surgery/procedures. The slotted, inverted-U-Shaped base plate, fits between the thighs of the patient bearing against the pubic bone area. The blades are angled and are equipped with a slotted opening in the handles, allowing the blades to be placed onto screws extending from the base plate. The blades can then be adjusted and tightened into place with a wing nut or similar fastener.

The retracting blades are generally L-shape with an upturned distal portion. The device operates in the manner of a clamp wherein the downward pressure of the base plate against the exterior surface of the pubic area applies an upward and outward pressure to the respective retracting blades. This clamping action holds the retractor securely in place, leaving Surgical Assistants available at all times for their primary duties of aiding the Surgeon. This will also reduce the number of Assistants required for these procedures.

Therefore, a primary object of the present invention is to provide a self-retaining vaginal retractor which does not obstruct a Surgeon's operating space.

Another primary object of the present invention is to provide a self-retaining vaginal retractor which simplifies successful dilation of the vaginal cavity for surgical and nonsurgical procedures, A related object of the present invention is to provide an upper and side blade self-retaining vaginal retractor which is small and easy to use for gynecological procedures.

An object of the present invention is to provide a self-retaining vaginal retractor which will maintain itself in position without being held manually.

An object of the present invention is to provide a self-retaining vaginal retractor which is adjustable to the anatomy of the patient.

An object of the present invention is to provide a self-retaining vaginal retractor which will eliminate the need for assistants whose sole task is to hold retractors.

A related object of the present invention is to provide a self-retaining vaginal retractor which will reduce costs associated with vaginal procedures.

Specifically, an object of the present invention is to provide a self-retaining vaginal retractor which will reduce cost by reducing the number of assistants required for vaginal procedures.

An object of the present invention is to provide a self-retaining vaginal retractor which can be adjusted during a procedure.

An object of the present invention is to provide an upper and side blade self-retaining vaginal retractor which allows independent vertical and horizontal adjustment of each retracting blade.

These and other objects and advantages of the present invention, along with features of novelty appurtenant thereto, will appear or become apparent in the course of the following descriptive sections.

BRIEF DESCRIPTION OF THE DRAWINGS

In the following drawings, which form a part of the specification and which are to be construed in conjunction therewith, and in which like reference numerals have been employed throughout wherever possible to indicate like parts in the various views.

DETAILED DESCRIPTION

Figure 1:
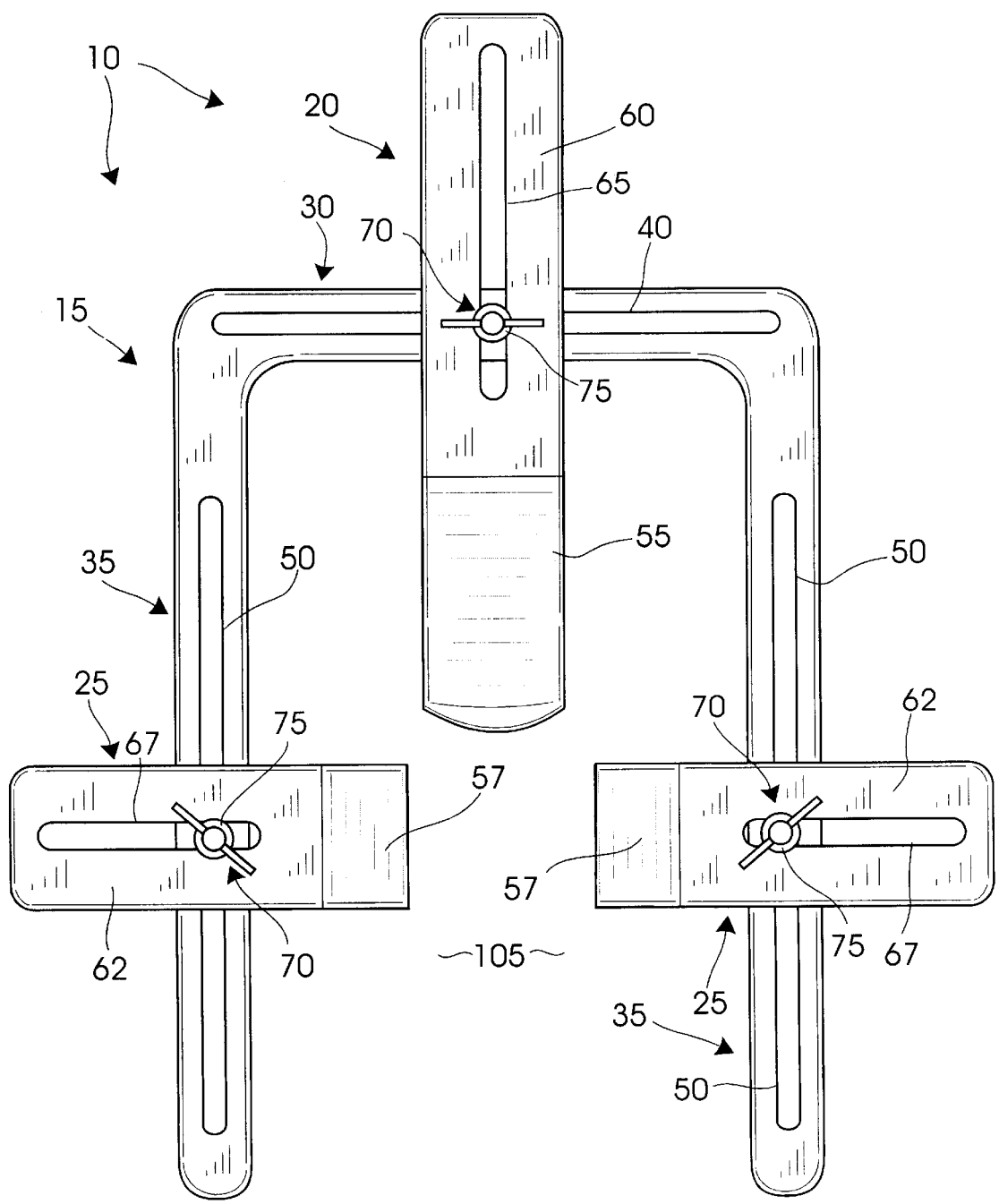
FIG. 1 is a front elevational view of a my self-retaining vaginal retractor, fully assembled.
Figure 2:
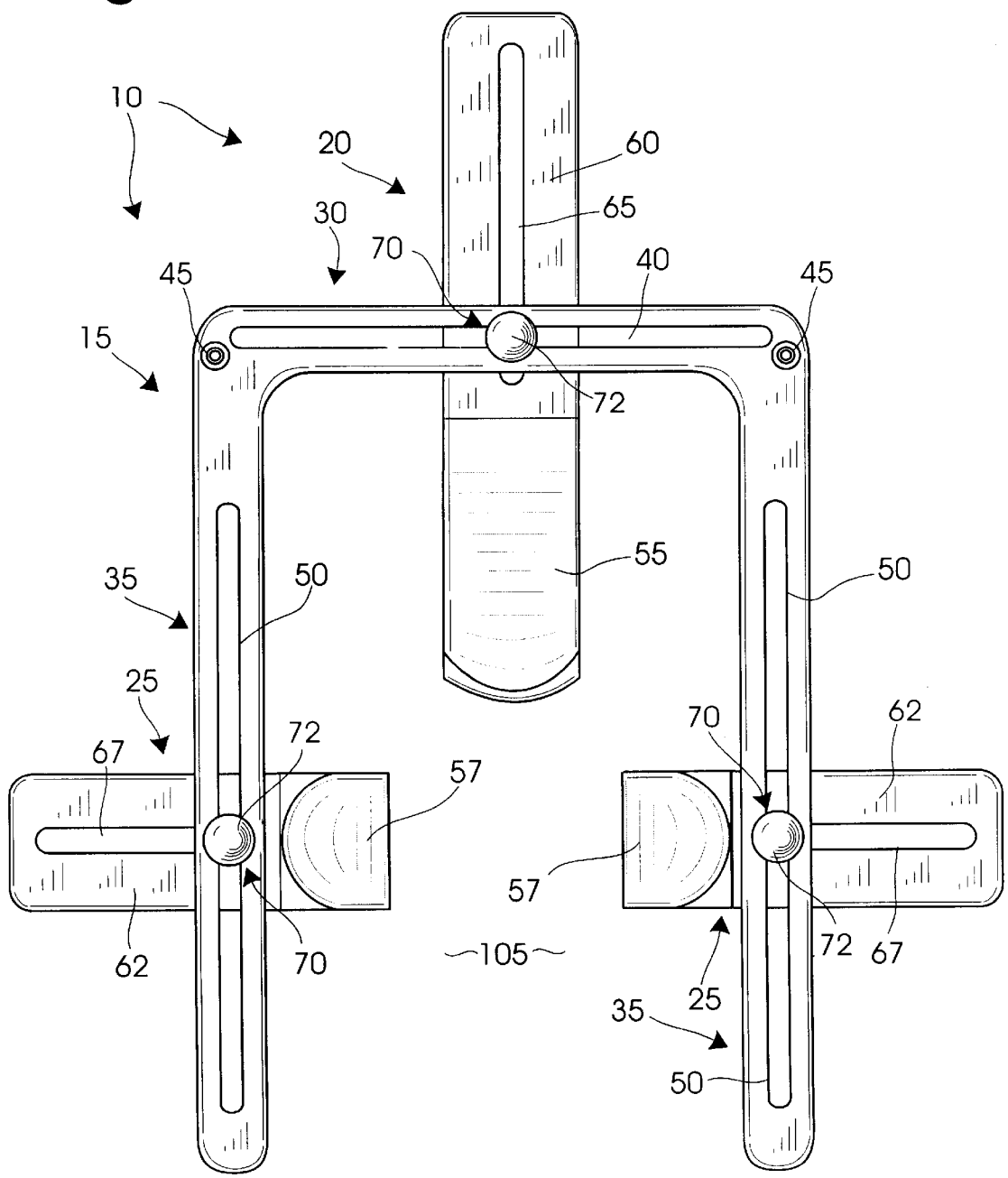
FIG. 2 is a rear elevational view of my retractor.
Figure 3:
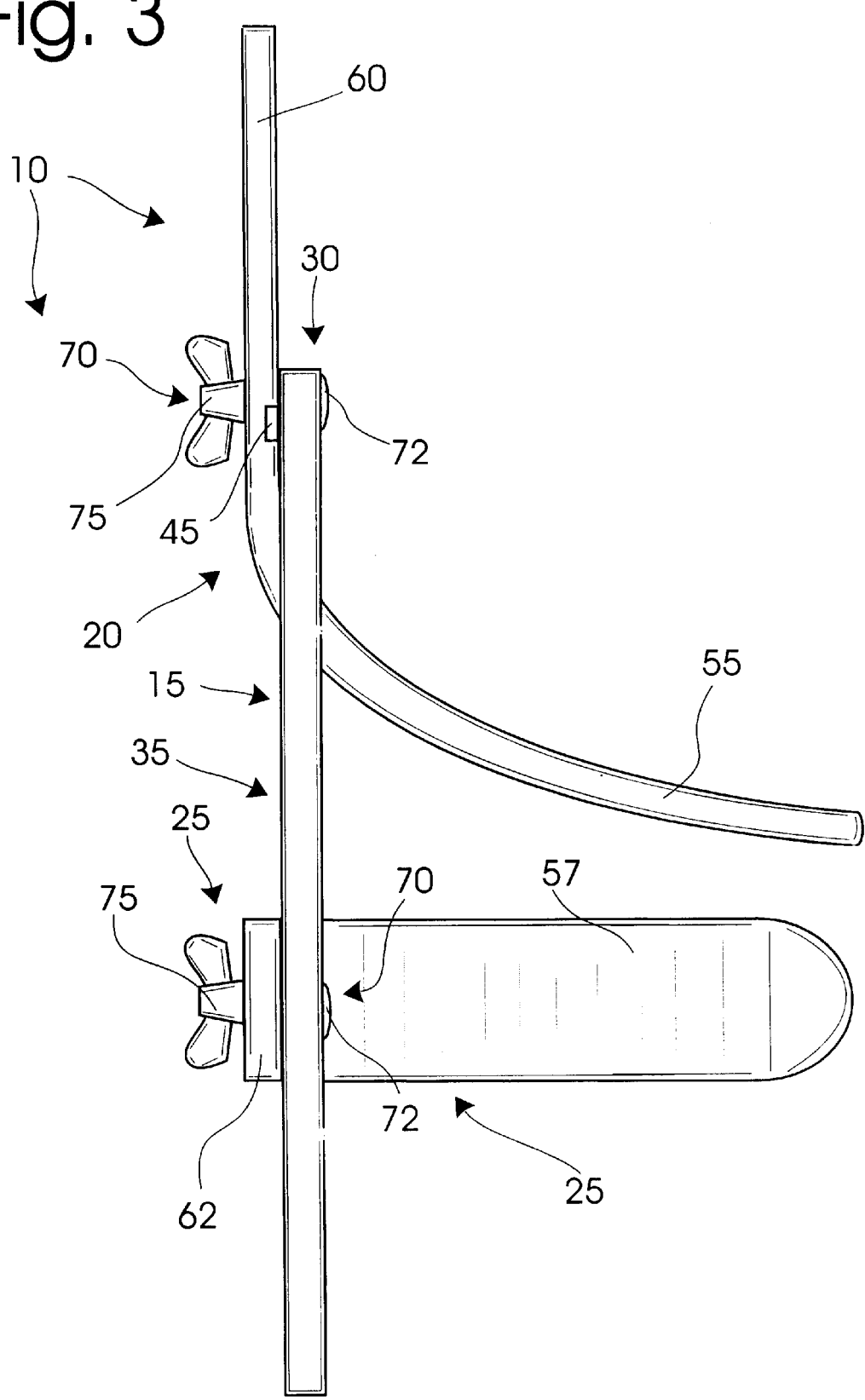
FIG. 3 is a side elevational view of my retractor.
Figure 4:
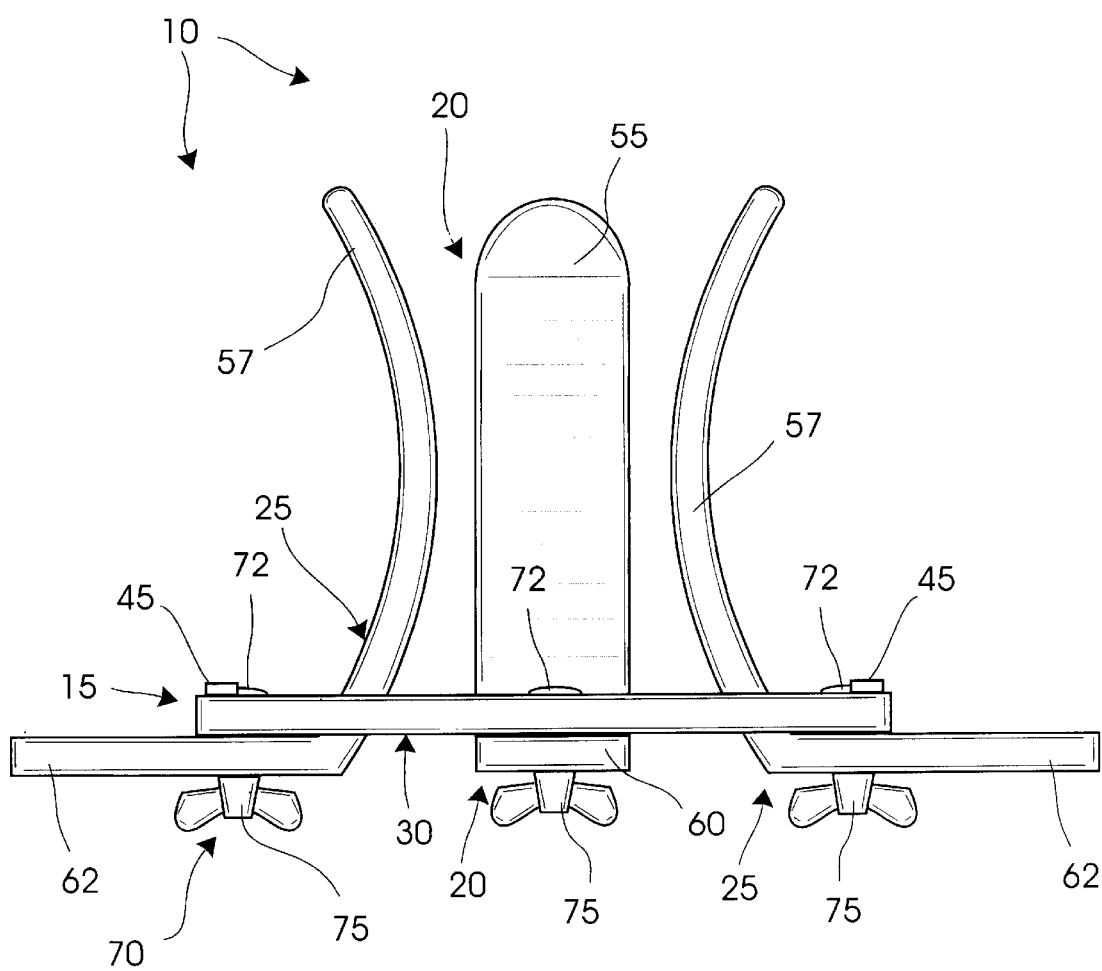
FIG. 4 is a top plan view of my retractor.
Figure 5:
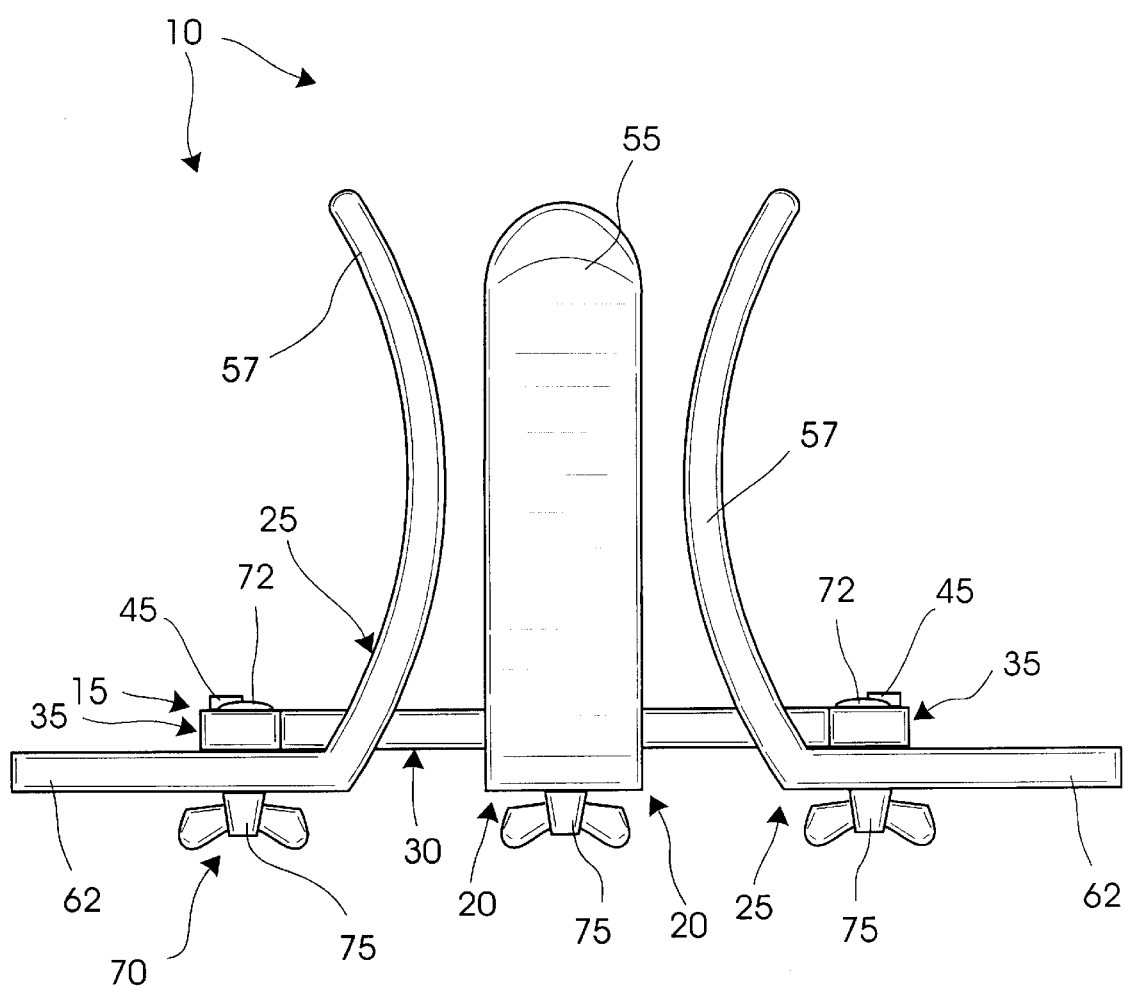
FIG. 5 is a bottom plan view of my retractor.
Figure 6:
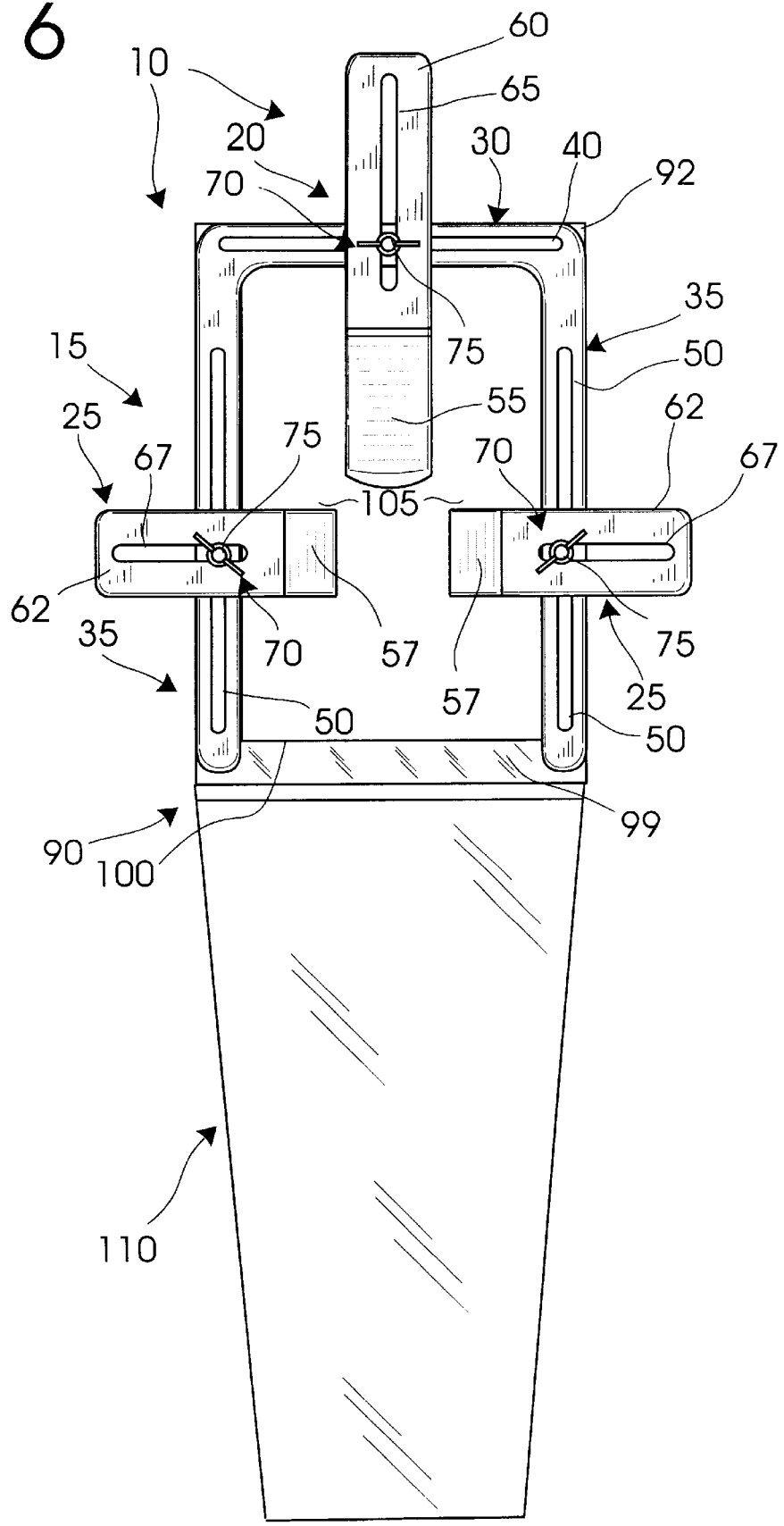
FIG. 6 is a front elevational view of my retractor with the bag in place.
Figure 7:
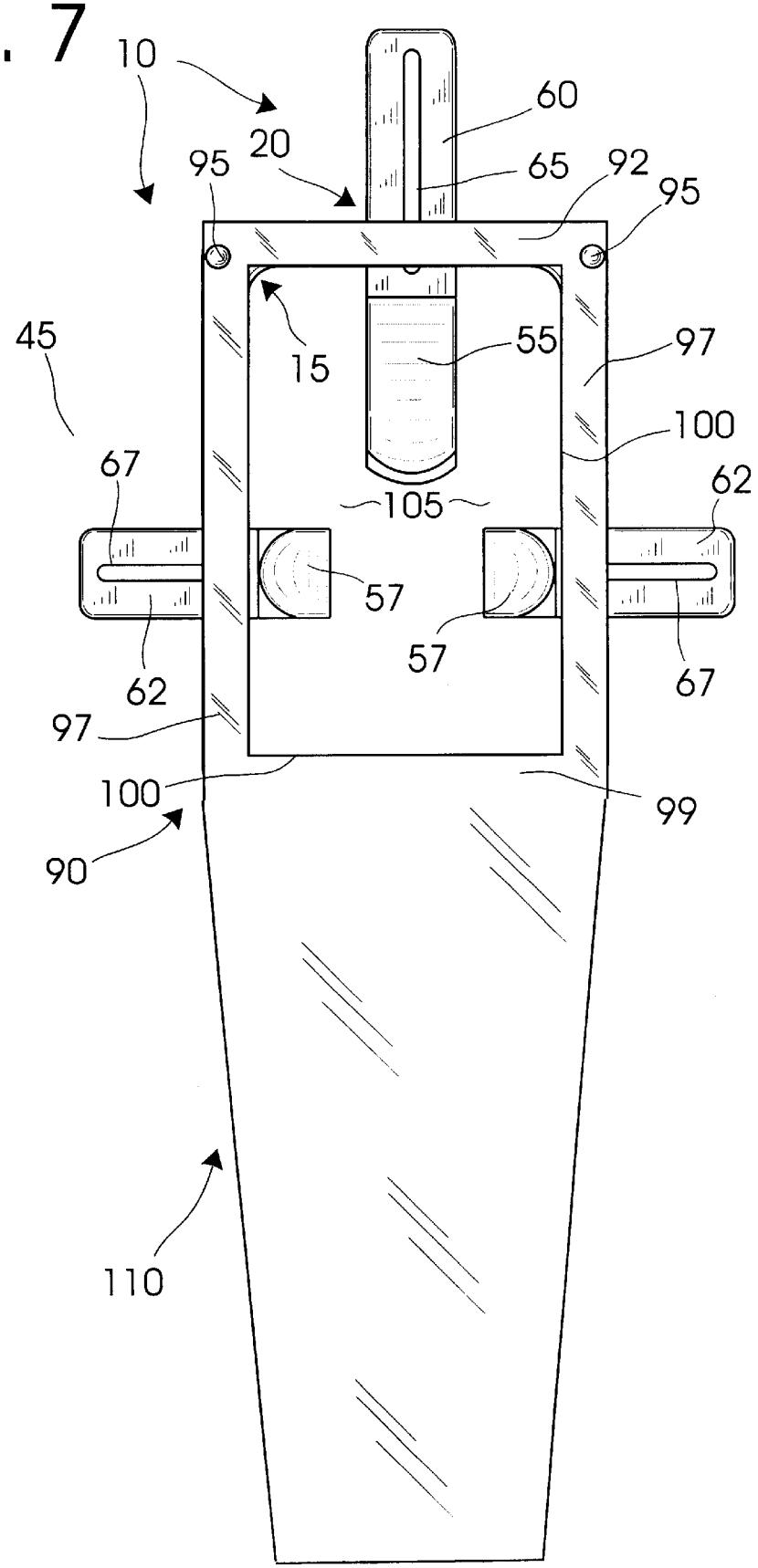
FIG. 7 is a rear elevational view of my retractor with the bag in place.
Figure 8:
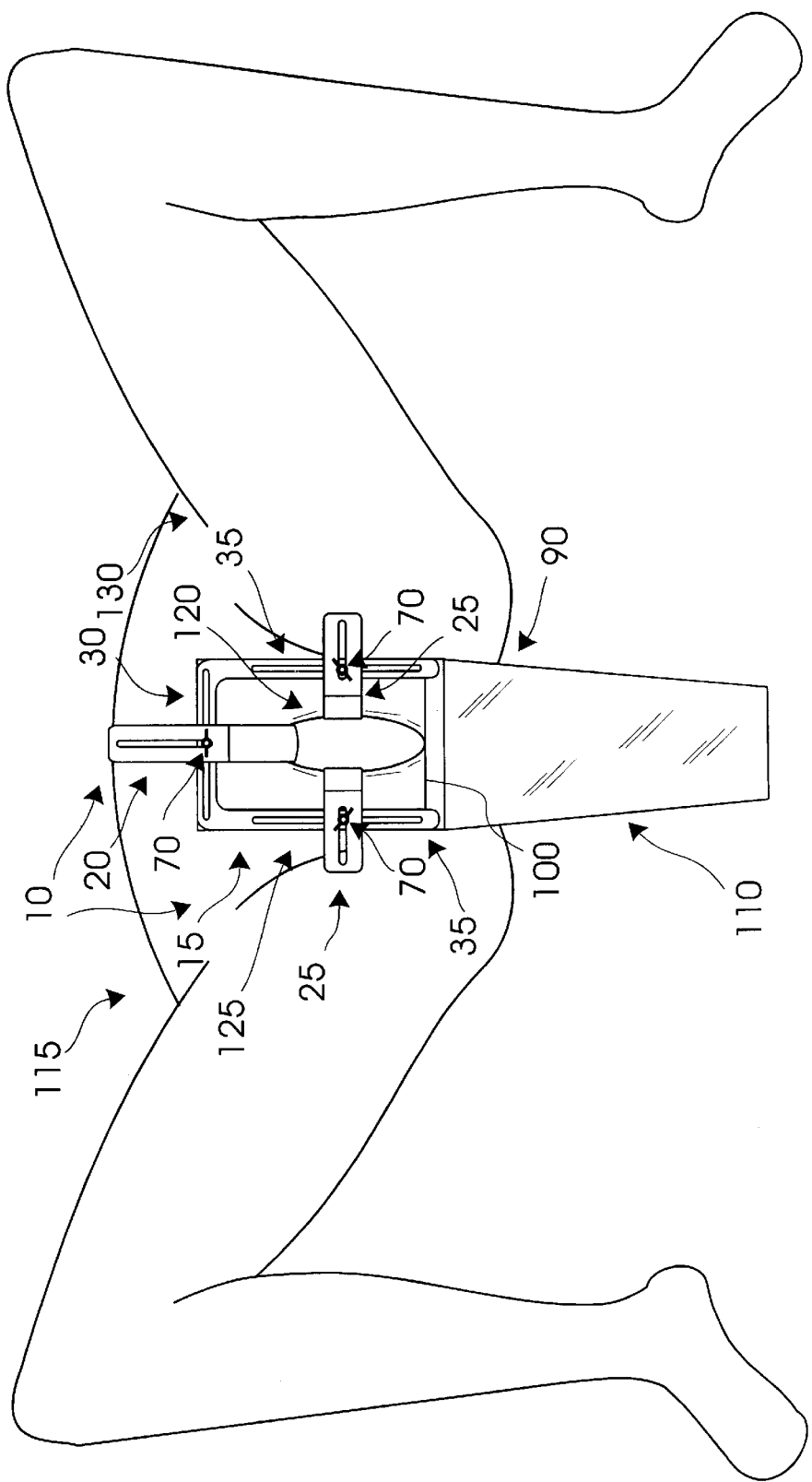
FIG. 8 is an environmental view of my retractor deployed on a patient who is disposed in the lithotomy position.

With reference now to the accompanying drawings, the preferred embodiment of my self-retaining vaginal retractor is broadly designated by the reference numeral 10. My self-retaining vaginal retractor 10 generally comprises a base plate 15 or frame having an inverted, generally U-shape. The base plate 15 selectively, adjustably mounts a top vagina retracting blade 20 and a pair of cooperating side vagina retracting blades 25.

The base plate 15 is comprised of a generally horizontal upper member 30 and a pair of spaced apart, generally parallel side legs 35 extending perpendicularly downward from the upper member 30. A generally horizontal slot 40 is defined through the upper member 30. A set of snap fasteners 45 are mounted to the back of the upper member 30 near the top of the base 15. Each of the base legs 35 define a generally vertical slot 50.

The top vagina retracting blade 20 and the side vagina retracting blades 25 are selectively, removably and adjustably secured to the base plate 15. The top retracting blade 20 to the upper member 30; and the side retracting blades 25 to the base legs 35. The integral retracting blades 20 and 25 each have a curved tongue portion 55 and 57 and a handle portion 60 and 62. The handle portions 60 and 62 define longitudinal slots 65 and 67 to receive an adjustably tensionable fastener 70 extending through the slots 40 and 50 of the upper member 30 and legs 35 of the base plate 15. Preferably, these adjustably tensionable fasteners 70 each take the form of a carriage bolt or similar screw 72 extending through and indexing with a slot 40 or 50 of the base plate 15 and a wing nut 75 used to secure the vagina retracting blade 20 and 25 in place. The wing nuts 75 are readily adjustable to allow the position of the retracting blades 20 and 25 to be adjusted during and following initial deployment of the retractor 10. The tongue portion 55 and 57 of the retracting blades extend from the handle portion 60 and 62 at an angle. The angle between the tongue 55 and handle 60 of the top retracting blade 20 is generally obtuse. Whereas, the tongue 57 and handle 62 of the side retracting blades 25 are generally disposed at a right angle to one another.

The preferred embodiment also employs a bag 90 selectively removably secured to the snap fasteners 45 on the back of the upper member 30. The bag 90 comprise a top generally horizontal portion 92 adapted to coincide with the upper member 30 of the base plate 15. The top portion 92 of the bag mounts snap fasteners 95 adapted to engage the snap fasteners 45 of the upper member 30. The bag 90 further comprises a pair of spaced apart, generally vertical side portions 97 extending downwardly from the horizontal portion 92, coinciding with the legs 35 of the base plate 15. A lower bag portion 99 extends across the lower extent of the side portions 99; thereby defining an opening 100 coinciding with the open area 105 defined between the legs of the base plate 15. An upwardly opening, downwardly tapered pouch 110 extends downward from the lower portion 99 of the bag 60. The pouch 110 is adapted to hold the vagina retracting blades 20 and 25 and adjustable fasteners 70, 72, and 75 prior to and during assembly of the retractor 10. During initial assembly of the retractor 10, the snaps 95 of the bag 90 are secured to the snaps 45 of the base plate 15. Thusly, the bag 90 is deployed under the base plate 15 of the retractor 10 between the patient 115 and the retractor 10 to collect irrigation fluids, body fluids and debris in the pouch 110.

Preferably, the base plate 15, blades 20 and 25, fasteners 70 and snaps 45 are made of surgical stainless steel or an equivalent material suitable for repeated sterilization. The edges of these components are smooth and/or rounded to insure safety and integrity of sterile fields. The bag 90 is preferably made from a durable plastic material with the bag's snaps 95 being made from stainless steel or plastic as needed to securely mate with the snaps 45 of the base plate 15. The bag is intended to be disposed of following use. Alternatively, the base plate 15, blades 20 and 25, fasteners 70 and snaps 45 may be made from a rigid plastic or similar material, and may be intended for disposal after use.

The retractor 10 simplifies successful dilation of the vaginal cavity 120 for surgical and nonsurgical procedures. The retractor 10 is sterilized prior to use. To deploy the retractor 10 the patient's legs 125 are flexed in the lithotomy position as for any conventional vaginal surgery/procedure. The patient's feet may be placed in stirrups or otherwise supported in an elevated position. The base plate 15, mounting the bag 90 and with the screws 72 deployed in the slots 40 and 50, is fitted between the thighs of the patient bearing against the pubic bone area 130. The base plate 15 is held in place by scrub personnel. The blades 20 and 25 are inserted into the vagina 120 of the patient and placed onto the screws 72 extending from the base plate 15. The blades 20 and 25 can then be adjusted up, down and side to side as necessary before or during the procedure.

Thus deployed the retractor 10 operates in the manner of a clamp, wherein the downward pressure of the base plate 15 against the exterior surface of the pubic area applies an upward and outward pressure to the respective vagina retracting blades 20 and 25. This clamping action holds the retractor 10 securely in place.

From the foregoing, it will be seen that this invention is one well adapted to obtain all the ends and objects herein set forth, together with other advantages which are inherent to the structure.

It will be understood that certain features and subcombinations are of utility and may be employed without reference to other features and subcombinations. This is contemplated by and is within the scope of the claims.

As many possible embodiments may be made of the invention without departing from the scope thereof, it is to be understood that all matter herein set forth or shown in the accompanying drawings is to be interpreted as illustrative and not in a limiting sense. For example, the use of a variety of materials to construct the present invention is anticipated.

What is claimed is:

1. A self-retaining vaginal retractor comprising:
    an inverted generally U-shaped base plate, said base plate comprising a generally horizontal upper member and a pair of spaced apart, generally parallel side legs extending perpendicularly downward from said upper member;
    a top vagina retracting blade removably and adjustably secured to said upper member, generally perpendicular to said upper member, said top retracting blade adjustable along said upper member and perpendicular to said upper member; and
    a plurality of cooperating side vagina retracting blades, each removably and adjustably secured to one of said base plate legs, generally perpendicular to said base plate legs, said side retracting blades adjustable along said base plate legs and perpendicular to said base plate legs.

2. A self-retaining vaginal retractor as defined in claim 1 further comprising a bag selectively removably secured to said base plate, said bag, comprising:
    a generally horizontal top portion adapted to coincide with said upper member;
    a pair of spaced apart, generally vertical side portions extending downwardly from said top portion, said side portions adapted to coincide with said legs; and,
    a lower portion extending downwardly from said side portions, said lower portion comprising a pouch adapted to hold said retracting blades and to catch debris and fluid.

3. A self-retaining vaginal retractor as defined in claim 1 wherein said retracting blades each comprise a curved tongue portion and an integral handle portion.

4. A self-retaining vaginal retractor as defined in claim 3 wherein each of said handle portions of said retracting blades define a longitudinal slot.

5. A self-retaining vaginal retractor as defined in claim 4 wherein said upper member and each of said legs of said base plate define a slot.

6. A self-retaining vaginal retractor as defined in claim 5 wherein said retracting blades are selectively, removably and adjustably secured to said base plate by ajustably tensionable fasteners extending through said slots defined in said base plate and said handles.

7. A self-retaining vaginal retractor as defined in claim 6 wherein said adjustably tensionable fasteners comprise a carriage bolt indexed to one of said slots in said base plate and extending through one of said slots in said blade handles and a wing nut threaded onto said carriage bolt.

8. A self-retaining vaginal retractor as defined in claim 6 further comprising a bag selectively removably secured to said base plate, said bag comprising:
    a generally horizontal top portion adapted to coincide with said upper member;
    a pair of spaced apart, generally vertical side portions extending downwardly from said top portion, said side portions adapted to coincide with said legs; and,
    a lower portion extending downwardly from said side portions, said lower portion comprising a pouch adapted to hold said retracting blades and adjustable fasteners and to catch debris and fluid.

9. A self-retaining vaginal retractor as defined in claim 8 wherein said adjustably tensionable fasteners comprise a carriage bolt indexed to one of said slots in said base plate and extending through one of said slots in said blade handles and a wing nut threaded onto said carriage bolt.

10. A self-retaining vaginal retractor as defined in claim 9 further comprising a plurality of snap fasteners secured to said upper member of said base plate; and a plurality of coinciding, cooperating snap fasteners secured to said top portion of said bag, said snap fasteners selectively, removably securing said bag to said base plate.

11. A self-retaining vaginal retractor comprising:
    an inverted generally U-shaped base plate, said base plate comprising:
        a generally horizontal upper member, said upper member defining a generally horizontal lateral slot; and,
        a pair of spaced apart, generally parallel side base plate legs extending generally perpendicularly downward from said upper member, each of said legs defining a generally vertical longitudinal slot;
    a top vagina retracting blade selectively, removably and adjustably secured to said upper member, generally perpendicular to said upper member by an adjustably tensionable fastener extending through said lateral slot, said top retracting blade comprising a curved tongue portion and an integral handle portion, said handle comprising a lengthwise slot to receive said adjustably tensionable fastener; and, a pair of cooperating side vagina retracting blades, each of said side blades selectively, removably and adjustably secured to one of said base plate legs, generally perpendicular to said base plate legs, by an adjustably tensionable fastener extending through said longitudinal slot, each of said side retracting blade comprising a curved tongue portion and an integral handle portion, said handle portion comprising a lengthwise slot to receive said adjustably tensionable fastener.

12. A self-retaining vaginal retractor as defined in claim 11 wherein said adjustably tensionable fasteners comprise a carriage bolt indexed to one of said slots in said base plate and extending through one of said slots in said blade handles and a wing nut threaded onto said carriage bolt.

13. A self-retaining vaginal retractor as defined in claim 11 further comprising a bag selectively removably secured to said base plate, said bag comprising:

a generally horizontal top portion adapted to coincide with said upper member;

a pair of spaced apart, generally vertical side portions extending downwardly from said top portion, said side portions adapted to coincide with said legs; and, a lower portion extending downwardly from said side portions, said lower portion comprising a pouch adapted to hold said retracting blades and adjustable fasteners and to catch debris and fluid.

14. A self-retaining vaginal retractor as defined in claim 13 wherein said adjustably tensionable fasteners comprise a carriage bolt indexed to one of said slots in said base plate and extending through one of said slots in said blade handles and a wing nut threaded onto said carriage bolt.

15. A self-retaining vaginal retractor as defined in claim 13 further comprising a plurality of snap fasteners secured to said upper member of said base plate; and a plurality of coinciding, cooperating snap fasteners secured to said top portion of said bag, said snap fasteners selectively, removably securing said bag to said base plate.

16. A self-retaining vaginal retractor as defined in claim 15 wherein said adjustably tensionable fasteners comprise a carriage bolt indexed to one of said slots in said base plate and extending through one of said slots in said blade handles and a wing nut threaded onto said carriage bolt.

17. A self-retaining vaginal retractor comprising:

an inverted generally U-shaped base plate, said base plate comprising:

a generally horizontal upper member, said upper member defining a generally horizontal lateral slot and mounting a plurality of spaced apart snap fasteners; and, a pair of spaced apart, generally parallel side base plate legs extending generally perpendicularly downward from said upper member, each of said legs defining a generally vertical longitudinal slot;

a top vagina retracting blade selectively, removably and adjustably secured to said upper member, generally perpendicular to said upper member by an adjustably tensionable fastener extending through said lateral slot, said top retracting blade comprising a curved tongue portion and an integral handle portion, said handle comprising a lengthwise slot to receive said adjustably tensionable fastener;

a pair of cooperating side retracting blades, each of said side retracting blades selectively, removably and adjustably secured to one of said base plate legs generally perpendicular to said base plate legs by an adjustably tensionable fastener extending through said longitudinal slot, each of said side retracting blades comprising a curved tongue portion and an integral handle portion, said handle portion comprising a lengthwise slot to receive said adjustably tensionable fastener; and, a bag selectively removably secured to said snap fasteners, said bag comprising:

a generally horizontal top portion adapted to coincide with said upper member, said top portion mounting a plurality of snap fasteners adapted to engage said snap fasteners mounted on said upper member;

a pair of spaced apart, generally vertical side portions extending downwardly from said top portion, said side portions adapted to coincide with said legs; and, a lower portion extending downwardly from said side portions, said lower portion comprising a pouch adapted to hold said retracting blades and adjustable fasteners and to catch debris and fluid.

18. The self-retaining vaginal retractor as defined in claim 17 wherein said adjustably tensionable fasteners comprise a carriage bolt indexed to one of said slots in said base plate and extending through one of said slots in said blade handles and a wing nut threaded onto said carriage bolt.

* * * * *